United States Patent [19]

Chakrabarti et al.

[11] Patent Number: 4,818,532
[45] Date of Patent: Apr. 4, 1989

[54] BROMOPHOR COMPOSITION

[75] Inventors: Paritosh M. Chakrabarti, Pittsburgh, Pa.; Roger A. Crawford, Wadsworth; Robert H. Juda, Akron, both of Ohio

[73] Assignee: PPG Industries, Inc., Pittsburgh, Pa.

[21] Appl. No.: 922,375

[22] Filed: Oct. 23, 1986

[51] Int. Cl.$^4$ ............................................. A61K 33/18
[52] U.S. Cl. ..................................... 424/150; 514/770
[58] Field of Search ......................... 424/150; 514/770

[56] References Cited

U.S. PATENT DOCUMENTS

| | | | |
|---|---|---|---|
| 2,679,533 | 5/1954 | Darragh et al. | 260/567.6 |
| 2,759,869 | 8/1956 | Sutton et al. | 167/70 |
| 2,868,686 | 1/1959 | Shelanski et al. | 167/17 |
| 3,067,089 | 12/1962 | Winslow | 167/17 |
| 3,277,010 | 10/1966 | Schenck et al. | 252/106 |
| 3,907,720 | 9/1975 | Field et al. | 260/2.5 R |
| 3,965,025 | 6/1976 | Klopotek et al. | 252/106 |
| 4,131,556 | 12/1978 | Klopotek et al. | 252/106 |
| 4,148,884 | 4/1979 | Thorogood | 424/150 |
| 4,444,756 | 4/1984 | Schlussler et al. | 424/150 |
| 4,526,751 | 7/1985 | Gartner | 422/37 |

FOREIGN PATENT DOCUMENTS

| | | |
|---|---|---|
| 107277 | 5/1984 | European Pat. Off. |
| 2525685 | 12/1976 | Fed. Rep. of Germany . |
| 110778 | 11/1981 | Poland . |
| 72/1556 | 3/1972 | South Africa . |
| 46/71 | 2/1971 | Zimbabwe . |
| 2537 | of 1889 | United Kingdom ................ 424/150 |
| 1237911 | 7/1971 | United Kingdom . |
| 1252774 | 10/1971 | United Kingdom . |
| 1275401 | 5/1972 | United Kingdom . |
| 1355359 | 5/1974 | United Kingdom . |
| 1357365 | 6/1974 | United Kingdom . |
| 1467614 | 3/1977 | United Kingdom . |

OTHER PUBLICATIONS

Lactam Complexes of Bromine-Hydrogen Bromide, W. E. Daniels et al., J. Org. Chem., Feb. 1963, pp. 573-574.

Structural Chemistry of Donor-Accepted Interactions, Henry A. Bent, Chemical Review, vol. 68, pp. 587-648 (1968).

*Primary Examiner*—Leonard Schenkman
*Attorney, Agent, or Firm*—Irwin M. Stein

[57] ABSTRACT

Described are free-flowing particulate bromophor compositions of a siliceous carrier having absorbed therein from 1 to 80 weight percent of a bromophor that is a complex of (a) bromine, (b) alkali metal halide and (c) nonionic, anionic or cationic surfactant-type organic material.

16 Claims, No Drawings

BROMOPHOR COMPOSITION

DESCRIPTION OF THE INVENTION

The present invention relates to biocidal bromine-containing compositions (bromophors). More particularly, this invention relates to a complex of bromine, halide ion and an organic carrier. Still more particularly, this invention concerns solid, free-flowing biocidal compositions of particulate amorphous siliceous carrier having the aforesaid complex absorbed thereon.

The halogens, i.e., chlorine, bromine and iodine, are recognized as excellent biocidal materials and are used extensively, particularly in the food processing and handling industries, to prevent bacteriological contamination of foodstuffs. Halogen sanitizers are also used in controlling potentially harmful organisms in potable water, swimming pools, hospitals, and wherever harmful organisms can present a contamination problem.

In order to utilize the sanitizing properties of the halogens and to eliminate or minimize many of the difficulties involved with their use in nascent form, complexes of halogen, particularly bromine and/or iodine, with organic carriers, e.g., surfactants, have been suggested. Bromine-containing complexes have been referred to as "bromophors", while iodine-containing complexes have been referred to as "iodophors". The sanitizing and germicidal activity of such "halophors" is derived essentially from the halogen which the halophor liberates.

Organic materials described in the art as carriers for halophors are varied. See, for example, British patent specification No. 1,357,365 which describes anionic, nonionic and cationic materials. This British specification also describes granular bromophor compositions in which the bromophor is sorbed onto a particulate, water-soluble, incompletely hydrated inorganic salt which forms stable hydrates. British patent specification No. 1,237,911, describes disinfectant compositions comprising a mixture of iodine, an ampholytic organoamino sulfonate, a nonionic surface active agent and a glycol. This composition is described as being adsorbed onto a silica and mixed with animal feed for controlling the growth of microorganisms within animals such as chickens, turkeys and pigs. The disinfectant compositions described in British patent specification No. 1,237,911 are not typical iodophors. They do not liberate iodine and do not exhibit the conventional starch-iodine reaction. The described compositions do not lose iodine even from boiling aqueous solutions but nevertheless are described as having disinfectant or antimicrobial activity, e.g., for in vivo applications.

Complexes of iodine with condensates of ethylene oxide and preformed poly(oxypropylene) glycol are disclosed in U.S. Pat. No. 2,759,869. Complexes of iodine monobromide with nonionic or anionic surface active agents are described in U.S. Pat. No. 2,868,686. Similarly, U.S. Pat. No. 4,131,556 describes forming a complex of iodine monobromide or the dibromine iodide ion, $[IBr_2]^-$, with nonionic surfactants such as fatty alcohols extended with ethylene oxide or alkylphenols extended with ethylene oxide. British patent specifications Nos. 1,252,774 and 1,355,359 describe complexes of bromine with nonionic surfactants, such as alkyl aryl polyalkyleneoxy alkanol surfactants, polyalkyleneoxy alcohols, polyalkylene oxide block copolymers and polyalkyleneoxy esters of fatty acids.

The present invention provides bromophor compositions which supply a source of bromine. The described compositions can be utilized for biocidal, e.g., sanitizing and disinfecting, applications. In those applications, the bromophor composition is commonly added to an aqueous media used to cleanse and sanitize the surfaces to be treated. The bromophor releases bromine in the aqueous medium, thereby forming hypobromite ion, and/or hypobromous acid, which serves as the biocidal agent. In accordance with the present invention, there is contemplated a composition comprising a free-flowing, particulate, inert, amorphous siliceous carrier having a biocidal amount of the bromophor of the present invention admixed therewith. The siliceous carrier is water-insoluble and has the bromophor adsorbed thereon. The bromophor comprises a complex of bromine, halide ion, e.g., alkali or alkaline earth metal halide, such as bromides or iodides, and an organic carrier.

DETAILED DESCRIPTION OF THE INVENTION

Organic carriers used to prepare bromophors of the present invention may vary and will depend upon the intended use of the bromophor, the properties of the bromophor desired, such as viscosity, miscibility, toxicity, cost, etc. Generally, to be useful, the organic carrier must form a complex with elemental bromine and be miscible with and preferably capable of at least partially dissolving (more preferably totally dissolving) the metal halide, e.g., sodium bromide, lithium bromide or potassium bromide (or their corresponding iodides or chlorides), or the bromides, chlorides and iodides of calcium and magnesium. The complex formed should liberate bromine under conditions of use in amounts sufficient to kill the biotic form; e.g., algae, bacteria, fungi, insect, etc., exposed to the complex.

Many different types of organic carriers that form complexes with bromine have been disclosed. Principally, those organic carriers which are capable of developing intermolecular attractive forces between the bromine and an atom in the organic carrier are preferred. Of particular note are those organic carriers containing oxygen atoms that form intermolecular interactions with bromine thereby binding the bromine to the organic carrier. Such intermolecular attractive forces develop when two atoms of bromine become positioned next to atoms, e.g., oxygen atoms, in the organic carrier having the correct orientation and spacing. A discussion of intermolecular interactions is found in the article, "Structural Chemistry of Donor-Acceptor Interactions", by Henry A. Bent, *Chemical Review*, Vol. 68, pages 587–648 (1968).

Organic carriers that have received particular attention for use in the preparation of bromophors are surfactant-type materials, i.e., nonionic, anionic, and cationic compounds. Such materials are described in British patent specification No. 1,357,365, the disclosure of which is incorporated herein by reference. As indicated, any of such organic compounds or materials, which are capable of developing intermolecular attractive forces with bromine, thereby forming a complex between the organic carrier and bromine atoms, may be used and are contemplated for use herein as an organic carrier. The organic carrier should also be capable of carrying the complexed bromine into aqueous solution without its precipitation or crystallization therein. Mixtures of organic carriers described herein may also be used.

Particular classes of nonionic surfactants which may complex bromine to form bromophors are:

1. Polyalkyleneoxy alkyl phenols,
2. Polyalkyleneoxy alcohols, and
3. Polyalkyleneoxy esters of fatty acids The polyalkyleneoxy alkyl phenols may be represented by the formula:

$$R_1-\phi-O-(R'O)_nH$$

wherein $R_1$ is an alkyl group containing from 5 to 30, more particularly 8 to 18, carbon atoms, e.g., octyl and nonyl, $\phi$ is phenylene, n is any number from about 1 to 100 and R'O is either ethylene oxide or a mixture of ethylene oxide with other alkylene oxides having from 3 to 4 carbon atoms such that the oxygen/carbon ratio in the $(R'O)_n$ hydrophilic group exceeds 0.4.

Some polyethyleneoxy alkyl phenol surfactants which may be utilized are:

1. t-octyl phenoxy polyethyleneoxy ethanol having the formula:

$$C_8H_{17}\phi O(CH_2CH_2O)_aH$$

in which $\phi$ is phenylene and a is a number from 1 to 40.

2. Dodecyl phenoxy polyethyleneoxy ethanol having the formula:

$$C_{12}H_{25}\phi O(CH_2CH_2O)_bH$$

in which $\phi$ is phenylene and b is a number from 10 to 18.

3. Branched chain nonyl phenoxy polyethyleneoxy ethanol having the formula:

$$C_9H_{19}\phi O(CH_2CH_2O)_cH$$

in which $\phi$ is phenylene and c is a number from 1 to 100.

4. Straight chain (linear) nonyl phenoxy polyethyleneoxy ethanol having the formula:

$$CH_3(CH_2)_8\phi O(CH_2CH_2O)_dH$$

in which $\phi$ is phenylene and d is a number from 1 to 15.

The polyalkyleneoxy alcohols may be represented by the formula:

$$R_2O(R'O)_eH$$

wherein $R_2$ is an alkyl group having from 6 to 32, preferably 8 to 22, e.g., 10 to 18, carbon atoms, a phenyl group or phenyl substituted with 1, 2 or 3 alkyl groups, which alkyl groups have a total of from 6 to 36 carbon atoms, e is any number from 2 to 50, e.g., 2 to 12, and R'O is as defined above.

One group of such surfactants are the alkyl polyethyleneoxy ethanols, more particularly, the linear primary alcohol polyethyleneoxy ethanols. This group of compounds may be represented by the formula:

$$CH_3-(CH_2)_m-CH_2-O-(CH_2CH_2O)_eH$$

wherein m is any number from 9 to 13 and e is any number from 2 to 50.

A second group of alkyl polyethyleneoxy ethanols are the secondary alcohol polyethyleneoxy ethanols. This group can be represented by the formula:

$$\begin{array}{c}CH_3-(CH_2)_p-CH_3\\|\\O-(CH_2CH_2O)_eH\end{array}$$

wherein p is any number from 8 to 16 and e is any number from 2 to 50.

The polyethyleneoxy esters of fatty acids can be represented by the formula:

$$R_5COO(R'O)_aH$$

wherein $R_5$ is an alkyl group having from 7 to 23 carbon atoms, R'O is as defined above and a is a number from 1 to 40. Particularly useful are those esters wherein $R_5$ is an alkyl group containing 10 to 18 carbon atoms, R' is ethylene and a ranges from 5 to 40.

Another group of nonionic carriers that may be used to prepare bromophors are monohalides of polyethoxylated phenols and polyethoxylated aliphatic alcohols represented by the following general formula, $R_6(OCH_2CH_3)_eX$, wherein $R_6$ is an alkyl group containing 8 to 22 carbon atoms, a phenyl group or phenyl group substituted in the ring with 1, 2, or 3 alkyl groups, which alkyl groups contain from 6 to 36 carbon atoms, and e is any number from 2 to 50. See, for example, U.S. Pat. No. 3,277,010.

Cationic surfactants that may be used to prepare bromophors may be represented by the following graphic formula:

$$\left[\begin{array}{cc}R_7 & R_8\\ \diagdown & \diagup\\ & W\\ \diagup & \diagdown\\ R_9 & R_{10}\end{array}\right]^+ X^-$$

wherein at least one of the radicals $R_7$, $R_8$, $R_9$ and $R_{10}$ is a hydrophobic aliphatic or araliphatic radical of from 1 to 28 carbon atoms, W is nitrogen or phosphorous and X is a salt-forming anionic radical, e.g., the chloride, bromide, iodide, sulphate, phosphate or acetate ion. The hydrophobic aliphatic or araliphatic radicals may be long-chain alkyl, short chain alkyl, long-chain alkoxyaryl, long-chain alkylphenoxyalkyl, long-chain alkylaryl, halogen substituted long-chain alkylaryl and arylalkyl groups. By the terms "short chain" or "lower", as used herein, is meant an alkyl group containing up to 7 carbon atoms, and by the term "long chain", as used herein, is meant an alkyl group containing from 8 to 22 carbon atoms. The remaining substituents on W, other than the hydrophobic aliphatic or araliphatic radicals, are hydrocarbon substituents containing a total of no more than 12 carbon atoms. The most suitable quaternary compounds are characterized by a molecular weight above 200.

Typical of the useful cationic surfactants are quaternary ammonium compounds. Quaternary ammonium compounds that may be used are those in which at least one of the radicals $R_7$, $R_8$, $R_9$ and $R_{10}$ attached to the nitrogen atom, W, is a hydrophobic aliphatic or araliphatic radical of preferably from 6 to 28 carbon atoms. The hydrophobic aliphatic or araliphatic radical may be long-chain, as herein defined, alkyl, long-chain alkoxyaryl, long-chain alkylaryl, halogen (chlorine, bromine, or iodine)-substituted long-chain alkylaryl, long-chain alkylphenoxyalkyl or arylalkyl. The term aryl includes phenyl and other aromatic groups. The remaining radicals on the nitrogen atom (other than the hydrophobic aliphatic or araliphatic radicals) are hydrocarbon substituents containing a total of no more than 12 carbon atoms. Such surfactants are disclosed more fully in U.S. Pat. No. 2,679,533. Examples of quaternary ammonium compounds are:

1. Alkylbenzyldimethylammonium halides.

The alkylbenzyldimethylammonium halides may be represented by the graphic formula:

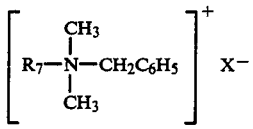

wherein $R_7$ may be an alkyl having from 8 to 18 carbon atoms and the phenyl group is unsubstituted or contains one or more halo substituents, and X is a chloride or bromide ion.

2. Alkyltrimethylammonium halides.

The alkyltrimethylammonium halides may be represented by the graphic formula:

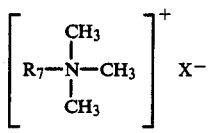

wherein $R_7$ may be an alkyl having from 8 to 18 carbon atoms, and X is a chloride or bromide ion.

Other cationic surfactants, to wit, quaternary phosphonium compounds, which may be used can be represented by the following graphic formula:

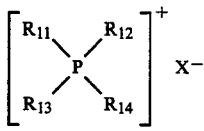

wherein at least one of the radicals $R_{11}$, $R_{12}$, $R_{13}$ and $R_{14}$ attached to the phosphorous atom is a hydrophobic aliphatic or araliphatic radical of from 1 to 28 carbon atoms. The hydrophobic aliphatic or araliphatic radicals may be long-chain, as herein defined, alkyl, long-chain alkoxyaryl, long-chain alkylaryl, halogen substituted long-chain alkylaryl, long-chain alkylphenoxyalkyl, and arylalkyl groups. The remaining substituents (other than the hydrophobic aliphatic or araliphatic radicals) are hydrocarbon substituents having from 1 to 28 carbon atoms. The radical X in the above formula may be any salt-forming anionic radical, as hereinabove described.

Anionic surfactants that may be used to prepare bromophors include the following organic anionic surfactants:

1. Phosphate esters,
2. Sulfonates, and
3. Carboxylates

The phosphate ester surfactants may be represented by the formula:

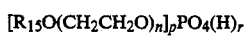

wherein $R_{15}$ is an alkyl, phenyl, alkylaryl or arylalkyl group containing from about 6 to about 30 carbon atoms, n is a number from 1 to 100, p is a number from 1 to 3, r is a number from 0 to 2 and p+r equals 3.

The sulfonated surfactants may be represented by the formula:

wherein $R_{15}$ and a are as hereinabove defined.

The carboxylate surfactants may be represented by the formula:

wherein $R_{15}$ and a are as hereinabove defined.

The halide ion used in the preparation of bromophors contemplated herein is typically provided by bromides of the alkali metals, e.g., sodium, lithium, or potassium, or the alkaline earth metals, e.g., calcium or magnesium, although other halides, e.g., iodides and chlorides, may be used. These metal halides may be represented by the formula MY, wherein M is hydrogen, an alkali or alkaline earth metal and Y is univalent iodine, bromine or chlorine, e.g., MBr, MCl or MI.

The amount of alkali or alkaline earth metal halide used to prepare the bromophor can vary. In general, the mole ratio of halide ion to elemental bromine in the bromophor, e.g., bromide:bromine ($Br^-:Br_2$), may vary from about 1:1 to about 1:12, more usually from 1:1 to 1:3. Preferably, the mole ratio is from about 1:1–1:2. Depending on the halide (bromide, chloride or iodide) ion used, the bromophor may contain one or more of the following halide or interhalide species: $Br_3^-$ and $Br_2$ multiples thereof, e.g., $Br_5^-$, $Br_7^-$, $Br_9^-$ etc; $Br_2I^-$ and $Br_2$ multiples thereof, e.g., $Br_4I^-$, $Br_6I^-$ etc.; $Br_2Cl^-$ and $Br_2$ multiples thereof, e.g., $Br_4Cl^-$, $Br_6Cl^-$, etc.

Bromine used to prepare bromophors contemplated herein is usually utilized in liquid form. However, if desired, the anhydrous vapor form of the bromine may be employed. Usually the amount of available elemental bromine present in the bromophor, i.e., $Br_2$, will vary from about 10 to about 50, e.g., 25 to 40, weight percent. By available bromine is meant that amount of bromine in the complex as determined by thiosulfate titration. Unavailable bromine is that bromine which combines irreversibly with the organic carrier and/or metal halide and is, hence, unavailable for sanitizing purposes—it is not released when the bromophor is placed into use as, for example, when it is incorporated into an aqueous medium.

The amount of available bromine present in a bromophor will depend primarily on the organic carrier utilized to form the complex. Some carriers are capable of complexing more bromine than others. Those bromophors which make available the largest amount of complexed bromine for sanitizing purposes are generally considered the most efficient and inexpensive to use. Depending on the organic carrier used, available bromine efficiencies may be in excess of 75 percent. In some instances, bromine efficiency exceeds 85 percent. By bromine efficiency is meant the percentage of available bromine present in the complex initially, i.e., at the time of bromophor preparation, based upon the total amount of elemental bromine used to prepare the bromophor.

Bromophors described herein may be prepared by combining the organic carrier, alkali metal or alkaline earth metal halide and bromine under suitable complexing conditions. Preferably, the organic carrier and source of bromide, chloride or iodide ion, more typically bromide ion, are first combined in a suitable reaction vessel to form a homogeneous mixture and preferably a uniform solution, and thereafter, bromine is introduced into the resulting reaction mixture. While not wishing to be bound by any particular theory, it is believed that the bromine added to the organic carrier-metal halide mixture reacts predominantly with the metal halide to form polyhalo species rather than reacting irreversibly with the organic carrier, thereby providing a product which yields significant quantities of available bromine for those applications requiring same. Preparation of the aforesaid complex of organic carrier, halide ion and bromine is performed, preferably in the substantial absence of water and more preferably under substantially anhydrous conditions. By substantial absence of water is meant that the reaction mixture contains less than 5 weight percent, preferably less than 2 weight percent, of total water, i.e., either intentionally added water or water present in the reactants. In particular, the bromophor is prepared in the presence of less than 1.0 weight percent total water, more particularly, less than 0.5, and still more particularly less than 0.1, weight percent total water.

As described, it is preferred that the reactants used to prepare the bromophor are substantially free of water, i.e., the organic carrier, metal halide source and bromine are substantially anhydrous. In the event that the aforesaid reactants, most notably the organic carrier and halide source contain significant quantities of water, they may be dried by contact with suitable drying agents, such as anhydrous sodium sulfate. Other conventional techniques for drying the precursor components that comprise the bromophor may also be employed. It is also contemplated that a particulate drying agent, such as anhydrous sodium sulfate, may be incorporated into the bromophor after it is prepared to remove small amounts of free water that may have been contained in the forming components and/or to retain the bromophor substantially free of moisture. It is, however, considered more desirable that the bromophor be prepared in the substantial absence of water rather than to remove water from the composition following its formation.

Conditions under which the bromophors are produced may vary depending on the particular composition being prepared. In the case of bromophors, it is preferred that liquid bromine be combined with a mixture, e.g., solution, of liquid organic carrier and metal halide. The reaction between liquid bromine and the organic carrier-metal halide liquid mixture is generally highly exothermic. Hence the reaction mixture should be vigorously stirred and cooled (by external cooling means if necessary) as the bromine is added slowly thereto. It is generally advisable to maintain the temperature of the reaction mixture from about 25° C. to about 55° C., more usually between 40° C. and about 50° C., for best results. Temporary temperature excursions outside the aforedescribed temperature range will yield satisfactory results provided that temperatures at which the halogen reacts irreversibly with the organic carrier are avoided for extended periods of time.

Organic carriers that are not liquids at or near room temperature, e.g., from about 18° C. to about 45° C., may be dissolved in a suitable organic solvent, such as methanol, and the bromophor prepared in solution. Subsequently, the solvent may be removed. Organic solvents that may be used are those which are inert, i.e., do not react chemically with the organic carrier or bromine which dissolve the metal halide, and which may be readily separated from the bromophor, e.g., by distillation. Organic carriers that have liquidus temperatures in the 25°–45° C. range may be heated to convert them to the liquid state for conversion to the bromophor.

In addition, stabilizers such as acids that are stable under the conditions of use, may be added to the bromophor. Some acids that have been suggested for use as stabilizers are hydrochloric acid, hydrobromic acid, phosphoric acid, and acetic acid.

The bromophor is admixed with a siliceous carrier to provide a composition having at least biocidal amounts of the bromophor. A biocidal amount is an amount that is sufficient to liberate a toxic dosage of elemental bromine, i.e., a dosage sufficient to kill at least 99 percent of the biologic population exposed thereto.

The siliceous carrier for the bromophor is an inert particulate amorphous siliceous material which is free-flowing and water-insoluble, i.e., has a water solubility at 20° C. of less than 0.5 grams per liter. The siliceous material is chemically inert with respect to the bromophor admixed therewith, i.e., the siliceous carrier does not react chemically with the bromophor.

The particulate siliceous carrier is of such size as is suitable for the intended use of the herein described bromophor composition as a biocidal agent. The particles, for practical purposes, are generally in the range of from 10 to 400 mesh (U.S. Standard Screen), i.e., in the size range of between $-10$ and $+400$ mesh, usually $-12$ or $-14$, $+325$ mesh. The siliceous carrier will typically have an oil absorption of between about 75 and 350 milliliters of dibutyl phthalate per 100 grams of silica. Oil absorption values can be obtained using a method like that described in ASTM D2414-65. For most applications, the oil absorption of the siliceous carrier will be between about 150 and 300 milliliters/100 grams.

The siliceous carrier may be a synthetic amorphous silica or naturally occurring silica- or silicate-containing material. Exemplary of synthetic amorphous silicas that may be used as the carrier are precipitated silica, fumed or pyrogenic silicas and silica gels, including hydrogels and aerogels. The aforesaid subcategories of synthetic amorphous silicas refer generally to the method of their preparation. Precipitated silicas are prepared by mixing an alkali metal silicate, e.g., sodium silicate, and a mineral acid, e.g., hydrochloric acid, sulfuric acid or carbonic acid, to cause precipitation of very fine silica particles which are washed free of residual alkali metal salts and dried. Precipitated silicas may be prepared by the methods described in U.S. Pat. No. 2,940,830. Fumed or pyrogenic silicas are generally prepared by the flame-hydrolysis of silicon tetrachloride to form a fine silica and by-product hydrochloric acid. Silica gel may be prepared by mixing an alkali metal silicate, e.g., sodium silicate, with a mineral acid at a pH and silica concentration such that a gelatinous precipitate (hydrogel) is formed. The hydrogel can then be washed to remove electrolytes either before or after drying, e.g., spray drying, and micronizing. When the hydrogel is dehydrated, an aerogel is formed. This is accomplished by displacing the hydrogel water prior to the drying step with a readily volatile material, e.g., an alcohol.

Precipitated silica particularly useful as a carrier for the halophor described herein is material having a BET surface area of between about 130 and about 180 square meters per gram, an oil absorption of between 200 and 270, e.g., between about 230 and 260, milliliters of dibutyl phthalate per 100 grams of silica, a water absorption of between about 160 and 180 milliliters per 100 grams of silica, a median agglomerate particle size of between about 6 and 15, preferably between 8 and 12, microns (micrometers), as measured by a Coulter counter, and a specific volume of at least 3.5 cubic centimeters per gram, e.g., 3.5–4.7 cm$^3$/g, when compacted with an applied pressure of 17 pounds per square inch (psi) (117 kPa).

Also contemplated for use as the siliceous carrier are naturally occurring silica- or silicate-containing minerals. These materials are rich in hydrated silicates of aluminum or magnesium and include such clays as montmorillonite, attapulgite, kaolinite, talc, bentonite, and Fuller's earth, diatomaceous earth, naturally occurring amorphous aluminum silicate (zeolites) and the synthetic zeolites, which are an amorphous combination of precipitated alumina and silica. Also contemplated for use as a carrier herein are precipitated calcium silicates, which include synthetic silicas containing small amounts, e.g., 1 to 10 percent, of calcium, calculated as calcium oxide. The above-described synthetic siliceous materials are generally commercially available or can be prepared by techniques known in the art.

The particulate bromophor-silica compositions of the present invention can be readily produced by admixing at least one siliceous carrier with the bromophor under conditions designed to obtain a homogeneous mixture. Liquid bromophors can be applied to the particulate siliceous carrier by spraying, preferably while the siliceous carrier is stirred or tumbled, to achieve uniform distribution of the bromophor on the carrier. Alternatively, the liquid bromophor can be poured onto the granular carrier and the mixture thereafter stirred. Generally, it is preferred to maintain the bromophor at temperatures of 55° C. or less to prevent irreversible reaction of the bromine with the organic carrier.

The amount of bromophor admixed with the siliceous carrier may vary widely and may be up to that amount which causes the carrier to lose its free-flowing property, i.e., up to the maximum absorptivity of the siliceous carrier utilized. Hence, the maximum amount of bromophor that can be sorbed by the siliceous carrier will be a function of its absorbtivity, i.e., its oil absorption. The higher the oil absorption value for a particular siliceous carrier—the greater is the amount of bromophor that can be retained by the carrier and still remain free-flowing.

The amount of bromophor sorbed onto the siliceous carrier is selected to provide a free-flowing, granular bromophor composition containing at least a biocidal amount of available bromine (or bromiodide). Since the amount of available bromine required for biocidal activity will vary with the end use, e.g., fumigant, sanitizer, or disinfectant, the quantity of bromophor sorbed onto the carrier may likewise vary and will also depend on the amount of bromine present in the bromophor available for the particular biocidal application.

It is contemplated that the siliceous carrier, depending on its absorbtivity, may contain from about 1 to about 80 weight percent of the bromophor, basis the weight of the siliceous carrier, e.g., between about 5 and 75, more usually between 10 and 40, weight percent of bromophor. For some applications between about 1 and 35 parts by weight of bromophor per 100 parts by weight of the siliceous carrier may be sufficient to provide a biocidal amount of available bromine.

It is contemplated that more than one amorphous, siliceous carrier may be used to prepare the particulate bromophor compositions of the present invention. Thus, mixtures of siliceous carriers may be used. It is further contemplated that particulate bromophor compositions containing high levels of bromophor (in the form of a masterbatch) may be prepared with highly absorptive siliceous carrier(s) and subsequently diluted with other chemically inert solid diluents, e.g., less absorptive (and perhaps less costly) siliceous carriers, clays, and inorganic, preferably water soluble, salts. Such particulate bromophor masterbatch compositions may contain from about 30 to about 80, e.g., 50 to 75, weight percent bromophor. Inorganic salts contemplated are alkali metal sulfates, phosphates, (orthophosphates and polyphosphates) carbonates and chlorides. The salts of sodium and potassium are preferred for most applications. Preferably, the salts are used in their anhydrous form.

The compositions contemplated herein may be added to water to produce solutions or dispersions containing a commercially useful and desired concentration of available bromine. Solutions containing from about 1.0 to 2000 parts per million of bromine are particularly useful for disinfecting or sanitizing surfaces. For example, they may be used by themselves or in combination with other cleaners and biocides for the cleaning of floors, walls, sinks, bowls, tanks, pasteurizers and pipes. In addition, solutions of bromophors may be applied to paper in the course of its manufacture to control mold and fungi.

The compositions of the present invention are more particularly described in the following examples which are intended as illustrative only since numerous modifications and variations therein will be apparent to those skilled in the art.

EXAMPLE I

A mixture of 1.64 parts of Neodol ®25–9 ethoxylated linear alcohol and 1 part of Neodol ®25–12 ethoxylated linear alcohol was prepared so as to approximate a Neodol ®25–10 ethoxylated linear alcohol having an average of 10 moles of ethylene oxide per mole of alcohol. 138.2 grams of the mixture was placed in a reaction flask and 21.8 grams of lithium bromide added thereto. The contents of the flask were heated to 85° C. to facilitate dissolution of the lithium bromide in the ethoxylated alcohol and then air cooled to 40° C. 12.9 milliliters (40 grams) of bromine were then added slowly over thirty minutes to the flask. The temperature of the reaction mixture rose initially to 49° C. The reaction mixture was cooled to 40° C. and bromine addition thereto continued with the temperature of the mixture being maintained in the range of 40°–46° C. A heating mantle was placed around the reaction flask to keep the reaction mixture warm. After 65 minutes the heat was turned off. The temperature of the reaction mixture had reached 48°–49° C. The reaction mixture—a viscous orange liquid—was cooled to 40° C., bottled, and stored at a constant temperature of 30° C. Periodically, a sample was removed and tested by thiosulfate titration for the amount of available bromine remaining in the stored product. Results are tabulated in Table I.

EXAMPLE II

A beaker was charged with 35.0 grams of a free-flowing, amorphous, precipitated silica having the following typical physical properties: BET Surface Area—260-290 square meters per gram; Oil Absorption—260-285 milliliters; pH—6.5-7.3; Median Particle Size—28 micrometers; and Particle Size Range—24-34 micrometers. To the beaker was added 65.0 grams of the product of Example I. The mixture was blended with a spatula until the mixture appeared uniform. The resulting blend was a free-flowing yellow powder. The powder was stored at a constant temperature of 30° C. Periodically, a sample was removed and tested for available bromine as described in Example I. Results are tabulated in Table I.

EXAMPLE III 69.1 grams of the synthetic Neodol®25-10 ethoxylated linear alcohol prepared in Example I and 69.4 grams of methoxypolyethylene glycol having a molecular weight of approximately 350 (Carbowax®350) were charged to a reaction flask and 21.8 grams of lithium bromide added to the mixture. The contents of the flask were heated to 88° C. to facilitate dissolution of the lithium bromide in the organic carrier mixture. The flask contents were cooled to 40° C. and 12.9 milliliters of liquid bromine added slowly over 25 minutes to the flask. The temperature of the reaction mixture was maintained generally in the range of 43°-47° C. The reaction product—a viscous orange liquid—was cooled to 25° C., bottled and stored at a constant temperature of 30° C. Periodically, a sample was removed and tested for available bromine, as described in Example I. Results are tabulated in Table I.

EXAMPLE IV

A beaker was charged with 35.0 grams of the silica powder described in Example II and 65.0 grams of the reaction product of Example III. The mixture was blended with a spatula until the mixture appeared uniform. The resulting blend was a free-flowing yellow powder. The powder was stored at a constant temperature of 30° C. Periodically, a sample was removed and tested for available bromine as described in Example I. Results are tabulated in Table I.

EXAMPLE V 65.0 grams of methoxypolyethylene glycol having a molecular weight of approximately 350 (Carbowax®350), 65.0 grams of an anionic organic phosphate ester (Gafac®RE-610), and 25.0 grams of lithium bromide were charged to a reaction flask and mixed. The temperature of the mixture rose from 20° C. to 50° C. The mixture was cooled to 45° C. and 30.6 milliliters (95.0 grams) of bromine added slowly to the mixture over an 80 minute period. The temperature of the reaction mixture was maintained at 50° C.±5° C. during bromine addition. The reaction mixture was stirred for 1.5 hours and the reaction product bottled. A portion was stored in a freezer. A portion of the reaction product was stored at a constant temperature of 30° C. and periodically tested as described in Example I.

EXAMPLE VI

A beaker was charged with 17.5 grams of the silica powder described in Example II and 32.5 grams of the reaction product of Example V that had been stored in a freezer. The amount of available bromine in the frozen sample of Example V was substantially the same as the originally prepared material. The mixture in the beaker was blended with a spatula until the mixture appeared uniform. The resulting blend was a free-flowing orange powder. The powder was stored at a constant temperature of 30° C. Periodically, a sample was removed and tested for available bromine as described in Example I. Results are tabulated in Table I.

TABLE I

| Time, Wks. | Wt. % Available Bromine Example No. | | | | | |
| --- | --- | --- | --- | --- | --- | --- |
| | I | II | III | IV | V | VI |
| Start | 17.9 | 11.7 | 18.0 | 11.9 | 27.8 | 17.7 |
| 3 days | 17.6 | 11.4 | 18.4 | 11.8 | 28.3 | 16.6 |
| 1 | 17.8 | 11.2 | 17.9 | 11.6 | 28.3 | 17.0 |
| 2 | 17.8 | 10.9 | 17.4 | 11.3 | 25.9 | 16.6 |
| 3 | 17.2 | 10.9 | 17.6 | —* | 25.5 | —* |
| 4 | 17.0 | 10.8 | 17.4 | 11.2 | 24.6 | 16.1 |
| 6 | 16.6 | 10.5 | 17.6 | 11.2 | 24.2 | 15.8 |
| 9 | 16.8 | 10.2 | 17.4 | 11.0 | 23.6 | 16.3 |

*No reading taken

The data of Table I show that the silica-bromophor compositions of Examples II, IV and VI are relatively stable, vis-a-vis the bromophor compositions of Examples I, III and V—the difference in initial available bromine concentrations being a dilution effect of the siliceous carrier.

Although the present invention has been described with reference to specific details of certain embodiments thereof, it is not intended that such details should be regarded as limitations upon the scope of the invention except as and to the extent that they are included in the accompanying claims.

What is claimed is:

1. A free-flowing particulate bromophor composition comprising particulate, inert amorphous siliceous carrier and from about 1 to about 80 weight percent of a bromophor that is a complex of (a) bromine, (b) halide represented by the formula MY, wherein M is hydrogen, alkali metal or alkaline earth metal, and Y is bromine, chlorine or iodine, the mole ratio of halide to bromine being from about 1:1 to 1:12, and (c) organic carrier capable of developing intermolecular attractive forces with bromine, the organic carrier being selected from nonionic, anionic and cationic surfactant-type materials, the amount of bromine in the bromophor being between about 10 and about 50 weight percent.

2. The composition of claim 1 wherein the siliceous carrier is a synthetic amorphous silica, or naturally occurring silica- or silicate-containing mineral.

3. The composition of claim 2 wherein the siliceous carrier contains from about 10 to about 40 weight percent of bromophor.

4. The composition of claim 1 wherein the siliceous carrier is amorphous precipitated silica.

5. The composition of claim 2 wherein the organic carrier is a nonionic surfactant-type material.

6. The composition of claim 5 wherein the organic carrier is selected from the group consisting of polyalkyleneoxy alkyl phenols, polyalkyleneoxy alcohols, polyalkyleneoxy esters of fatty acids, monohalides of polyethoxylated phenols and monohalides of polyethoxylated aliphatic alcohols.

7. The composition of claim 2 wherein the organic carrier is a cationic surfactant-type material.

8. The composition of claim 7 wherein the organic carrier is a quaternary ammonium or quaternary phosphonium compound.

9. The composition of claim 2 wherein the organic carrier is an anionic surfactant-type material.

10. The composition of claim 9 wherein the organic carrier is an organic phosphate ester, organic sulfonate or organic carboxylate.

11. A free-flowing particulate bromophor composition comprising particulate, inert amorphous siliceous carrier and from about 1 to about 80 weight percent of a bromophor that is a complex of (a) bromine, (b) halide represented by the formula MY, wherein M is hydrogen, alkali metal or alkaline earth metal, and Y is bromine, chlorine or iodine, the mole ratio of halide to bromine being from about 1:1 to 1:12, and (c) nonionic organic surfactant-type carrier that is capable of developing intermolecular attractive forces with said bromine, the amount of bromine in the bromophor being between about 10 and about 50 weight percent.

12. The composition of claim 11 wherein the organic carrier is selected from the group consisting of polyalkyleneoxy alkyl phenols, polyalkyleneoxy alcohols, polyalkyleneoxy esters of fatty acids, monohalides of polyethoxylated phenols and monohalides of polyethoxylated aliphatic alcohols.

13. The composition of claim 12 wherein the siliceous carrier is a synthetic amorphous silica, or naturally occurring silica- or silicate-containing mineral.

14. The composition of claim 13 wherein the siliceous carrier is amorphous precipitated silica.

15. The composition of claim 13 wherein the alkali metal is sodium, lithium or potassium, and the alkaline earth metal is calcium or magnesium.

16. The composition of claim 15 wherein the siliceous carrier is amorphous precipitated silica.

* * * * *